United States Patent [19]
Sandel

[11] Patent Number: 4,485,919
[45] Date of Patent: Dec. 4, 1984

[54] STERILIZABLE FOAM SUPPORT TRAY FOR MEDICAL INSTRUMENTS

[76] Inventor: Dan Sandel, 19524 Halsted St., Northridge, Calif. 91324

[21] Appl. No.: 598,244

[22] Filed: Apr. 9, 1984

Related U.S. Application Data

[63] Continuation of Ser. No. 407,447, Aug. 12, 1982.

[51] Int. Cl.³ ............................................. B65D 81/16
[52] U.S. Cl. .................................. 206/370; 206/523; 206/592; 206/820; 220/902; 428/35; 428/158; 428/167
[58] Field of Search ............... 206/338, 339, 340, 343, 206/346, 370, 523, 524, 563, 564, 587, 592, 820; 220/902; 428/157–164, 167, 35

[56] References Cited

U.S. PATENT DOCUMENTS

| | | |
|---|---|---|
| 2,282,908 | 5/1942 | Thompson . |
| 2,784,840 | 3/1957 | Stefanik . |
| 2,928,100 | 3/1960 | Gagnon . |
| 3,127,302 | 3/1964 | Gunting . |
| 3,136,679 | 6/1964 | Bender ............................ 206/455 |
| 3,221,872 | 12/1965 | Wood . |
| 3,285,768 | 11/1966 | Habib . |
| 3,626,616 | 12/1971 | Seme . |
| 3,690,452 | 9/1972 | Ungar . |
| 3,723,061 | 3/1973 | Stahl . |
| 3,733,657 | 5/1973 | Lankton . |
| 3,819,039 | 6/1974 | Erickson . |
| 4,093,010 | 6/1978 | Hunley et al. . |
| 4,146,132 | 3/1979 | Chiba . |
| 4,243,140 | 1/1981 | Thrun . |

FOREIGN PATENT DOCUMENTS

| | | |
|---|---|---|
| 2907253 | 9/1980 | Fed. Rep. of Germany . |
| 1341968 | 9/1963 | France . |

*Primary Examiner*—George F. Lowrance
*Assistant Examiner*—Jimmy G. Foster
*Attorney, Agent, or Firm*—Poms, Smith, Lande & Rose

[57] ABSTRACT

A sterilizable support tray for medical instruments is disclosed comprising a block of sterilizable reticulated foam material having multiple parallel longitudinally-extending and laterally-extending slices which penetrate partially through the thickness of the foam block. In addition to a verticle component, at least one of the slices includes a horizontal component for defining a plane and creating a reduced cross-section partable web attaching multiple finger portions created by said slices to an unsliced base portion. The partable webs define a location and plane at which individual finger portions may be torn away from the base portion to define custom-shaped channels within which medical instruments may be positioned, stored, sterilized, and accounted for.

4 Claims, 7 Drawing Figures

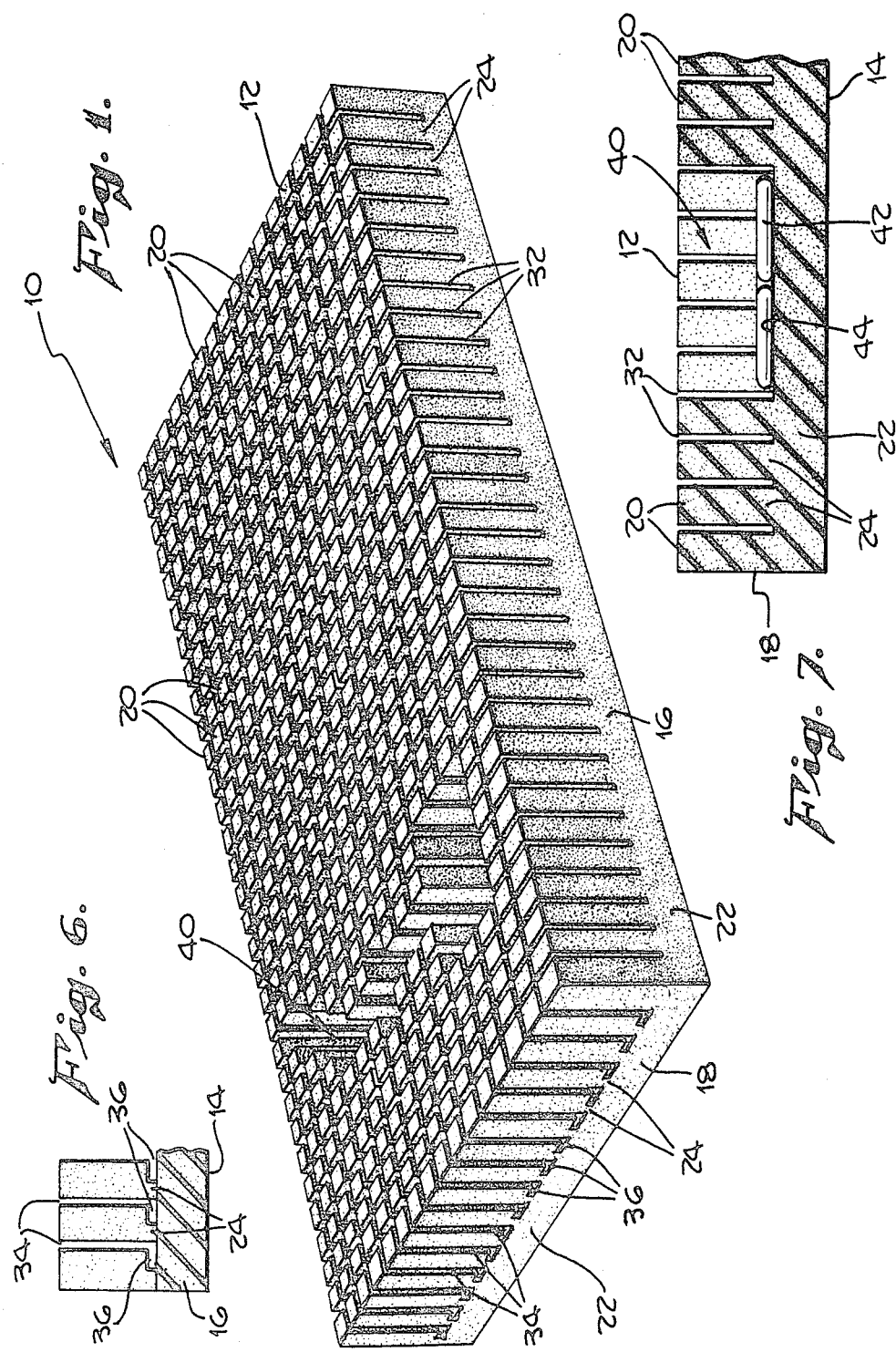

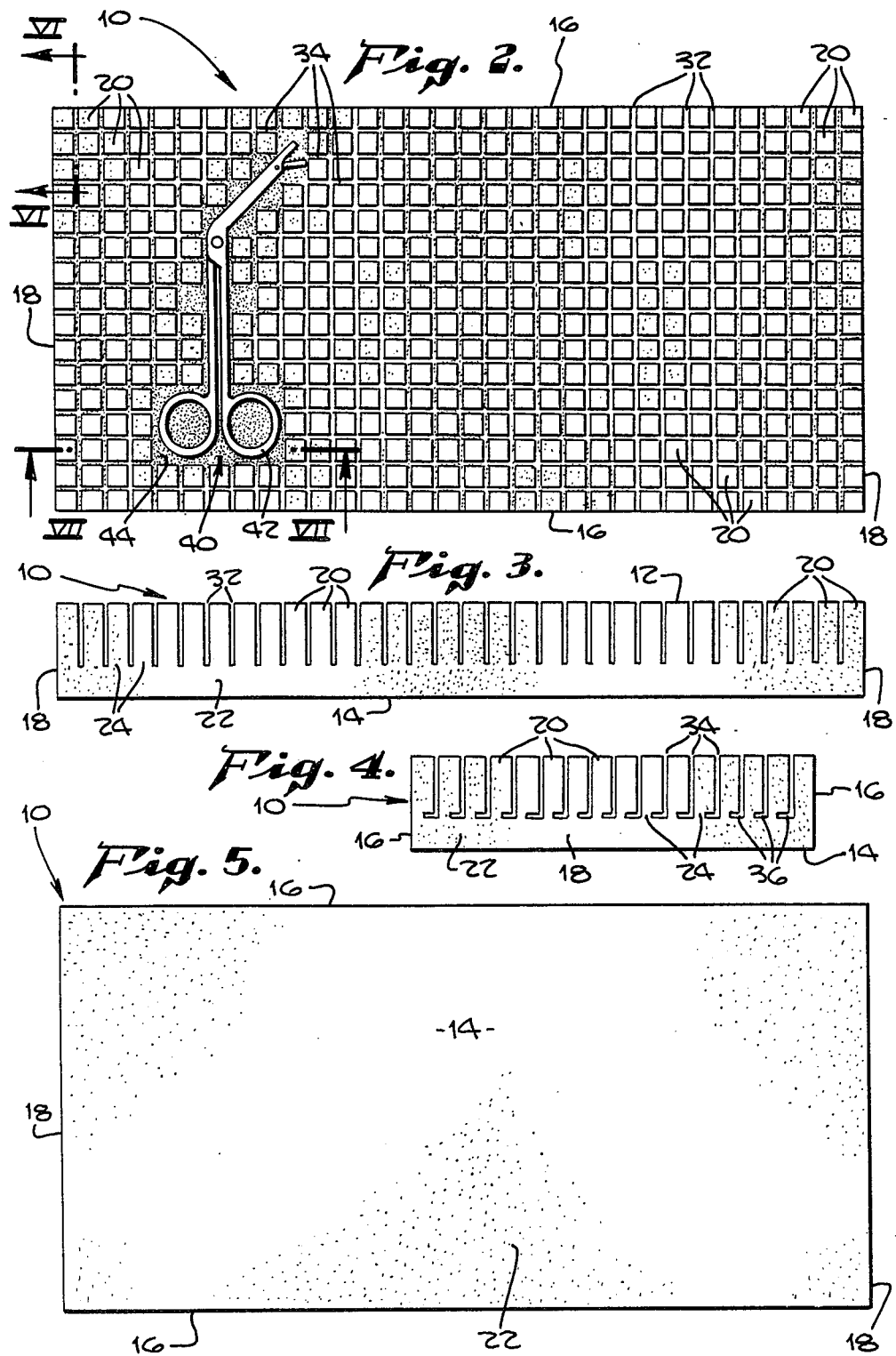

STERILIZABLE FOAM SUPPORT TRAY FOR MEDICAL INSTRUMENTS

This application is a continuation of application Ser. No. 407,447, filed Aug. 12, 1982.

The present invention relates in general to sterilizable foam trays for supporting medical instruments and, more particularly, to medical instrument supporting trays formed of sterilizable reticulated foam and having multiple detachable fingers for creating channels corresponding to the shape of the supported instrument.

BACKGROUND OF THE INVENTION

Foam has been used extensively as a packing and supporting material. In the surgical instrument field, foam has been provided in sheets and slabs as a base upon which medical instruments may rest and, in particular, the foam may be molded or carved during its manufacture into channels corresponding with the shape of the particular instrument being supported.

In the surgical supply field, reticulated foam has been known as a material which will withstand sterilization processes and resist the generation of particles in air suspension, dust, and other aerosols which might contaminate an operating room sterile field.

It is also generally known that in the packaging field, particularly for camera equipment, that slabs of foam material may be perforated or formed into multiple fingers which may be selectively cut and removed by the user to form custom-shaped channels to hold and contain that equipment. In one such example, these fingers are formed by a grid of intersecting slices cutting a preselected depth into a slab of foam material whereby multiple rows and columns of fingers are formed which may be cut-off at their base to create channels corresponding with the shape of the object intended to be held. One difficulty encountered in creating these customized channels was the difficulty in evenly and smoothly cutting off one of these foam fingers at its base in order to create a channel having a smooth and uniform bottom.

There has been a long-felt need in the surgical supply industry for an apparatus and method of positioning, storing, sterilizing, and accounting instruments used in surgery that may be easily and readily adapted to support and contain instruments of a variety of shapes and sizes associated with a selected surgical procedure.

Accordingly, it is an object of the present invention to create an easily-manufactured slab of foam which may be used within the sterile field of a hospital operating room which has easily detachable fingers for creating custom-shaped channels with a smooth and uniform bottom.

SUMMARY OF THE INVENTION

Simply stated, the present invention comprises a block of foam forming a generally rectangular solid and having a plurality of mutually parallel slices penetrating partially through the thickness of the foam block and extending in a first direction, and a second plurality of mutually parallel slices penetrating partially through the foam block and extending in a second direction intersecting the slices in the first direction thereby forming multiple fingers of foam, each of said fingers being attached to an integral foam base by a partable web having a cross-section smaller than that of the respective finger.

More specifically, a support tray for medical instruments is formed from a horizontally-extending generally-planar rectangular solid slab of reticulated and sterilizable foam material. The support tray is provided with a series of parallel, evenly spaced slices penetrating perpendicularly from the top surface of the slab to a uniform depth into the support tray. The support tray is further provided with a series of parallel, evenly spaced generally L-shaped slices having a vertical component which penetrates perpendicularly from the top surface to the same uniform depth into the support tray as the first-mentioned series of slices and oriented to intersect said slices to form multiple upward-extending fingers, and a horizontal component extending partially toward the vertical component of the next-adjacent slice leaving therebetween a partable web having a reduced cross-sectional area making the upward extending finger easily detachable in a predetermined manner.

By selectively detaching certain fingers, custom-shaped instrument holding channels may be formed in the support tray. In accordance with this feature, medical instruments may be easily supported, organized, and accounted for during surgery, sterilization and storage. Further, by operation of the partable web, these channels may be formed spontaneously without the use of a cutting tool.

In accordance with another embodiment of the present invention, the generally L-shaped slices can extend in both of the intersecting directions, and, alternatively, one or both of the slices may have a horizontal component in two directions, thereby forming a generally upside-down T-shaped slice.

By these improved forming techniques for use with reticulated foam, blocks of foam may be manufactured having easily-detached fingers and which are sterilizable and usable with medical instruments as a support tray. Other objects and advantages of the present invention may be more fully understood by one skilled in the art from a consideration of a detailed description of a preferred embodiment of the present invention taken in combination with the accompanying drawings as follows:

BRIEF DESCRIPTION OF THE DRAWINGS

FIG. 1 is a perspective view of the support tray of the present invention showing certain fingers removed to form a channel for supporting and storing a medical instrument.

FIG. 2 is a top view of the improved support tray of FIG. 1.

FIG. 3 is a side view of the improved support tray of FIG. 2.

FIG. 4 is an end view of the improved support tray of FIG. 2.

FIG. 5 is a bottom view of the improved support tray of FIG. 2.

FIG. 6 is an end section of a portion of the improved support tray of FIG. 2 taken in section along plane VI—VI of FIG. 2.

FIG. 7 is a side section of a portion of the improved support tray of FIG. 2 taken in section along plane VII—VII of FIG. 2.

DETAILED DESCRIPTION OF A PREFERRED EMBODIMENT

Referring to all of the drawings taken together, in a preferred embodiment, the present invention is formed from a single piece block of reticulated foam material in the shape of a rectangular solid, indicated generally at 10. The block of foam has a top surface 12, a bottom surface 14, two parallel side surfaces 16 and two parallel and surfaces 18.

The block of foam is modified in accordance with the present invention by the provision of two series of mutually parallel slices into the foam block for forming multiple finger portions 20 extending upward from a common integral base portion 22 and attached thereto by a partable web 24.

More particularly, the foam block 10 is first modified by a series of multiple mutually parallel slices 32 penetrating partially through the thickness of the foam block and extending in a first direction, which in the preferred embodiment is laterally.

In this preferred embodiment, each of the laterally extending slices 32 extends vertically downward perpendicular to top surface 12 to a uniform depth below which is left an unsliced base portion 22.

A second series of slices are provided having two components, namely mutually parallel vertical components 34 and co-planar horizontal components 36. Together, each horizontal component 36 and respective vertical component 34 define an L-shaped slice. The horizontal component 36 of each L-shaped slice extends proximate to the next adjacent L-shaped slice leaving a web portion 24 which has a reduced cross-sectional diameter relative to its respective finger portion 20 as defined by said two series of slices. The first series of slices extend laterally and the second series of slices extend longitudinally to together form a grid of independent removable finger portions having a square cross-section.

Each finger portion 20 is removable from base 22 at a predetermined position in a predetermined manner as defined by partable web 24 which connects the respective finger portion 20 to the base portion 22. An upward force on a finger portion 20 in excess of a preselected threshold level determined by the cross-section of the partable web 24 and the resistance to tearing of the reticulated foam material causes the partable web to be torn in such a manner that a substantially planar horizontal channel is left wherever a finger portion 20 is torn away. It is particularly contemplated that selected multiple finger portions 20 would be torn away from the multiple rows and columns of finger portions to create custom-shaped channels. The size and shape of medical instruments to be supported by and carried within these channels would be accomodated by the selective removal of certain finger portions 20. The resulting channel portions indicated generally at 40 thus have a generally-planar bottom surface 44 corresponding with the plane of the horizontal component 36 of each of the longitudinally extending slices thereby forming a base and confining walls defined by remaining fingers within which a medical instrument 42 may be positioned, secured, stored, sterilized and accounted for.

One optimal spacing of the series of mutually parallel lateral and longitudinal slices is with a one-half inch spacing between each vertical slice and penetrating to a depth of one-half inch such that multiple rows and columns of cubic finger portions are formed having a one-half inch dimension on each side. This dimension is best accomplished with a foam slab having a one-inch thickness such that the resulting base portion 22 forming the bottom of a channel 40 has a thickness of one-half inch. In another geometry, as particularly shown in the drawings, the multiple slices are again spaced one-half inch from one another, however the foam slab has a two-inch thickness and the slices are cut such that they penetrate through one and one-half inches of the thickness of the foam block, thereby, again, leaving a one-half inch thick base portion under an instrument channel 40. Optimal finger lengths providing adequate support for most surgical instruments while still being easily extracted from the support tray channel thus fall in the range between one-half and two and one-half inches inclusive.

The present invention has thus been described with regard to a preferred embodiment and drawings thereof. It should be apparent to one skilled in the art that various adapations and modifications of the present invention may be accomplished which still fall within the scope and spirit of the present invention. In particular, the dimensions utilized for the cross-section of the finger portions may range, for example, from one quarter of an inch to one inch by adjusting the spacing between the multiple parallel slices. Further, a planar arrangement of partable webs for each of the multiple finger portions can be defined by using an L-shaped slice, as described, in both the lateral and the longitudinal directions such that the partible web becomes located at a corner of a respective finger portion rather than at a side. Alternatively, each of the multiple component slices may further include a horizontal component in two directions rather than one, thereby forming a generally upside-down T-shaped slice usable in one or both of the slicing directions thereby forming each partable web portion at a central position with respect to each finger portion. Accordingly, the scope of the present invention is defined and limited only by the following claims.

I claim:

1. The method of forming an improved medical instrument support tray out of a block of sterilizable foam material comprising the steps of:

cutting a first series of multiple mutually-parallel slices in said block, said slices being perpendicular to said planar top surface extending along a substantial length of one axis of said block;

cutting a second series of multiple slices extending along a substantial length of a second axis of said block, forming a plurality of finger portions in said block; and under cutting each of a plurality of said finger portions a distance more than one half of their width from along one side thereof to provide an asymmetrically located reduced width web connection along an opposite side thereof and extending between the finger portions and adjacent portions of said block to facilitate removal of said finger portions from said block.

2. An improved medical instrument support tray comprising a slab of foam having a first series of multiple mutually parallel vertical slices penetrating partially through its thickness which extend in a first direction, said slab further having a second series of multiple slices penetrating partially through its thickness which extend in a second direction, said second series of slices each having a vertical component mutually parallel with the vertical component of the other slices of the second series and which intersect the first series of slices, and a horizontal component, said horizontal component extending partially toward but not intersecting the next adjacent slice of the second series whereby multiple finger portions are formed in the slab; said slab further having asymmetrical connecting means for attaching each of said multiple finger portions to a common base portion by an asymmetrically located reduced cross-section web lying generally along one edge of the associated finger portion.

3. The improved medical instrument support tray of claim 2 wherein said horizontal and vertical components of each of said second series of slices together define a substantially L-shaped slice.

4. The improved medical instrument support tray of claim 2 wherein the vertical component of both the first series and the second series of slices penetrate a uniform depth into the slab and wherein the lower edge of each of the slices taken together define a plane which is coplanar with the plane defined by the horizontal components of each of the second series of slices.

* * * * *